United States Patent [19]

Hartl et al.

[11] 4,225,557
[45] Sep. 30, 1980

[54] PACKAGED DIAGNOSTIC TEST STRIP

[75] Inventors: Roland Hartl, Eppertshausen; Dieter Helm, Heppenheim; Dieter Kraemer, Mainz, all of Fed. Rep. of Germany

[73] Assignee: Röhm GmbH, Darmstadt, Fed. Rep. of Germany

[21] Appl. No.: 915,263

[22] Filed: Jun. 13, 1978

[30] Foreign Application Priority Data

Jul. 1, 1977 [DE] Fed. Rep. of Germany ... 7720665[U]

[51] Int. Cl.² .................................................. G01N 33/16
[52] U.S. Cl. .......................................... 422/56; 422/58
[58] Field of Search ................ 23/253 TP; 422/56, 58

[56] References Cited

U.S. PATENT DOCUMENTS

| | | | |
|---|---|---|---|
| 3,001,915 | 9/1961 | Fonner | 422/56 |
| 3,443,903 | 5/1969 | Haack et al. | 23/253 TP X |
| 3,891,507 | 6/1975 | Breuer | 23/253 TP X |
| 3,901,657 | 8/1975 | Lightfoot | 23/253 TP |
| 3,980,437 | 9/1976 | Kishimoto et al. | 23/253 TP |
| 3,996,006 | 12/1976 | Pagano | 23/253 TP |

FOREIGN PATENT DOCUMENTS 51-8688   1/1976   Japan ..................... 23/253 TP

*Primary Examiner*—Arnold Turk
*Attorney, Agent, or Firm*—Curtis, Morris & Safford

[57] ABSTRACT

Packaged diagnostic test strip comprising a first or front sheet having at least one aperture therein, said aperture or apertures having at least one included angle equal to or less than 90 degrees; a diagnostic test strip under said front sheet and extending under said aperture or apertures, said test strip carrying a diagnostic reagent; a second or back sheet supporting said test strip in layered arrangement therewith and with said front sheet, said back sheet having at least one flap-covered aperture therein in that region thereof corresponding with the location of said aperture or apertures in said front sheet, whereby when the flap is open said test strip is exposed thereunder; and a closure flap at least partially extending over said front sheet and having closure means thereon for covering said aperture or apertures in said front sheet when in closed position.

3 Claims, 3 Drawing Figures

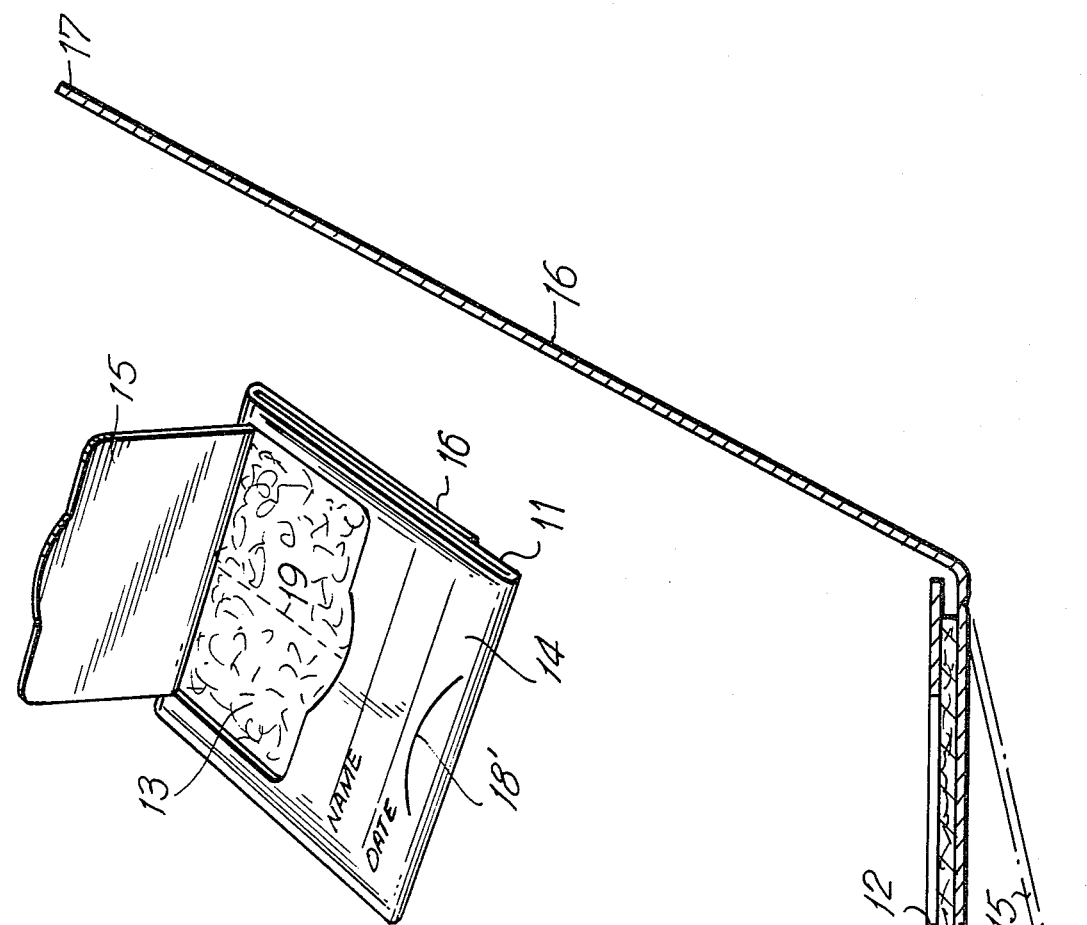
FIG. 1
FIG. 2
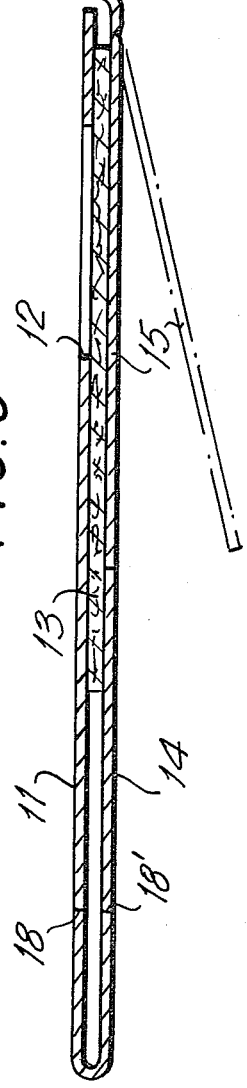
FIG. 3

PACKAGED DIAGNOSTIC TEST STRIP

The present invention relates to a packaged diagnostic test strip.

The need for a simple, quick, and sure diagnostic method has led in medicine to, among other things, the development of test strip methods. Test strips designed for the detection of occult blood in the stool serve as an example of test strip methodology. The test involves the demonstration of the blood component hemoglobin, which is peroxidase-active. In the presence of peroxide and under the influence of the peroxidase-effective hemoglobin, a series of suitable indicators will develop a recognizable color or color change. Advantageously, for example, guaicum resin, which gives a blue to blue-green coloration with peroxide in the presence of hemoglobin, is employed. Also, o-tolidine, which is oxidized to o-tolidine blue, shows such a reaction, as does 3,3',5,5'-tetramethyl-benzidine, which is oxidized to the corresponding dyestuff.

For the detection of occult blood in the stool, a filter paper strip which is saturated with guaicum solution or with a solution of another suitable indicator is used in principle, a sample of the stool to be tested is applied thereto, and the paper is "developed", for example by the addition of a peroxide solution.

Different proposals have been made for the packaging of test strips for stool analysis. In practice, for example, perforated packages with round "holes" for application of the stool sample are employed.

Thus, in U.S. Pat. No. 3,996,006, a test slide or package is proposed which comprises a front sheet having plural openings, a rear sheet, and an intermediate layer therebetween located under the aforementioned openings and which carries a test reagent. The package also has a cover flap suitable for partial coverage of the front sheet and the openings therein. The rear sheet further has hinged flaps in the region of the reverse side of the openings in the front sheet. These hinged flaps, when opened, reveal the underside of the intermediate layer. The arrangement further includes closure means, for example, a tab on the hinged cover with a corresponding round slit which goes through both the front sheet and the rear sheet. The intermediate layer which carriers the test reagent as a rule comprises a suitable filter paper which is prepared with the test reagent. The remaining parts of the test package are as a rule made of cardboard, but the use of this material is not critical to their function. Because of the presence of at least two openings, it is possible to examine portions from differing regions of the stool or simultaneously to employ different indicators in the test. The test is as a rule carried out by smearing a stool sample across the surface of one of the openings using a suitable object (e.g. a spatula). A sample from a different portion of a stool can be applied to the second opening in a similar way. This part of the test can be performed by the patient himself. After closure, i.e. by insertion of the tab on the cover flap into the slit, the test slide goes to the doctor. The latter opens the flaps on the back sheet and then applies the developer e.g. (peroxide solution) to the portions of the intermediate sheet, impregnated with the test reagent, which are so exposed and observes the results. When guaicum resin is employed as an indicator in a test for occult blood in the stool, a blue to blue-green coloration indicates a positive result.

Hereinafter, that side of the test strip to which the stool sample is applied will be designed as the "front side"; the other side will be designated as the "rear side". A material suitable for both the front sheet and the rear sheet of the package, which sandwich the test strip itself, is, for example, cardboard. Certain details of construction which have been found to be useful are common to all of the test packages introduced into practice. Evidently, the formation of the opening (the "hole" through which the stool sample is applied to the intermediate layer) in the form of a circle is one of the solidly entrenched details.

Although the specification of the aforementioned U.S. patent does not discuss this matter, it is evident from the drawings therein that here also several circular openings are provided.

The considerations which may have preceded the construction of these holes as circular openings may be, on the one hand, that it appeared easier to estimate and place a suitable amount of stool sample within a circular area when applying it on the front side and, on the other hand, that it appeared relatively easy to apply developer to the rear side in the development step in a drop-wise fashion in the center of a circle (translucent within its contours). On development a procedure is observed which, in its details, is similar to the development of a round filter chromatogram: the dyestuff formed in a positive reaction is transported by the liquid phase, which is comprised of the developer and any residual moisture in the stool sample, to the periphery of the expanding circle of solvent and in this way is diluted. This results in a certain difficulty. In a relatively weak reaction, the dye is so diluted that a clear judgment cannot be made concerning the outcome of the test. In this way, a region of low blood concentrations, which necessarily must be diagnostically detected in the stool, is pushed outside the sensitivity of the method.

It has now been found that the test strip method using a test package of the type described comprising a front sheet with plural openings (holes), a rear sheet, and an intermediate layer carrying the test reagent which lies therebetween and under the aforementioned openings, which package has one or more flaps on the rear sheet in the region of the back side of the openings, which flaps when opened expose the rear side of the intermediate layer in the region beneath the openings (holes), and which package has a cover flap adaptable to (partial) closing of the front sheet inclusive of the openings and having sealing means for sealing the cover flap over the test strip, makes possible a clearer recognition of the color reaction if the individual openings have at least one angle which is less than or equal to 90 degrees. Openings which have a geometrically regular form (forms with a high degree of symmetry) and which have at least one angle which is less than or equal to 90 degrees are preferred.

From a practical viewpoint, openings exclusively having right angles are particularly preferred, particularly openings in the form of a square. The improved recognizability is attributable to an unexpected effect. When the text strip method for determining occult blood in the stool is carried out using a test package having square openings according to the present invention, to be sure the dye formed is transported to the periphery of the circularly spreading developer (developer spot) just as in the manner of a round chromatogram. Nevertheless, in those segments of the periphery which spatially come closest to the angle or angles of the openings, there is a higher dyestuff concentration (in the sense of an enrichment) than there is in remaining segments of the periphery. The portions of greatest color intensity are in the direction of the (imaginary) line joining the point of application of the developer, which as a rule is identical with the midpoint of the opening (or that point of the opening which the eye recognizes as the center of whatever geometric form is involved) and the corners of the opening which are defined by the right or acute angle. Because of the described higher concentrations of dyestuff in those segments of the periphery of the developer spot which are spatially closest to the corners of the opening (the "hole"), a correct diagnosis can be more easily made. The described effect can be designated as "angular color intensification". The corners formed by the angle should be defined as sharply as possible in the material, for example by stamping the "holes" out of the material.

A better understanding of the present invention will be had by referring to the accompanying drawings showing a preferred embodiment of the present invention in the form of a packaged test strip for the detection of occult blood in the stool.

FIG. 1 is a perspective view of the top side of a packaged test strip according to the invention;

FIG. 2 is a perspective view of the bottom side thereof; and

FIG. 3 is a side sectional view taken above line 3—3 of FIG. 1.

The drawings show front sheet 11 of the package having openings 12 therein, under which intermediate layer 13 having a diagnostic reagent thereon (the test strip per se) is positioned and through which openings 12 one side of layer 13 is accessible, for example for the application of a stool sample thereto. Rear sheet 14, provided with flap 15, supports the underside of layer 13. This second side of layer 13 is accessible by lifting flap 15, for example for the application of a "developer" reagent thereto in completion of the stool diagnosis. Front sheet 11 can be covered with cover sheet 16 provided with tab 17 which is engageable with slits 18 and 18' in front sheet 11 and rear sheet 14 respectively.

The package embodiment illustrated is conveniently made of a single strip of a material such as carboard, folded around layer 13 to define cover flap 16, rear sheet 14, and front sheet 11. Layer 13 is suitably of filter paper impregnated with a reagent or reagents.

Openings 12 in front sheet 11 are fashioned to have at least one angle equal to or less than 90°, and in the embodiment illustrated have four such angles, defining a rectangular aperture.

Those openings in which all the surfaces exclusively have right angles have proved to be particularly suitable. The sides of such a rectangle should be at least 5 mm. in length and the total surface area should be at least 1 cm². The length of a side as a rule will not exceed 25 mm. Square openings have a side length of 12–20 mm, in particular 14–16 mm, are particularly preferred.

The regions of reagent-impregnated layer 13 which are respectively arranged under each of the two openings 12 can optionally be separated one from another by means of barrier 19 (cf. FIG. 2) suitably narrow and formed from an appropriate material which hinders the passage of the liquid phase. The application of the barrier material is best done during impregnation of layer 13. For example, glue, wax, or synthetic resins can be employed. The application of a barrier 19 is to be recommended if layer 13 is to be impregnated with two different test reagents for the detection of occult blood in a stool, for example with guaicum resin, on the one hand and with o-tolidine or with 3,3',5,5'-tetramethylbenzidine on the other.

Following the example of those embodiments which are already commercially available, the packaged test strip according to the invention preferably contains guaicum resin or o-tolidine as test reagents.

The use of the packaged test strips according to the present invention is not significantly different from the use of packaged test strips already known in the art. The directions for the use of commercially-available packaged test strips for the detection of occult blood in the stool, as described earlier herein, can be followed without modification when using the preferred embodiment according to the drawings.

From the point of view of diagnostically useful results, the packaged test strips according to the present invention are different from those known in the art. Providing that developer is applied on the reverse side of layer 13 to those areas thereof which correspond on the front side to the intersection of the diagonals A-D and B-C, the sites of greatest color intensity on development will lie in the direction of these diagonals A-D and B-C, shown in dotted lines in FIG. 1 for explanatory purposes.

As regards the detection of occult blood in the stool as an indicator for malign tumors the packaged diagnostic test strip of the present invention offers a particular advantage because its sensitivity is precisely in the desired range.

What is claimed is:

1. A packaged diagnostic test strip for determining occult blood in a stool sample, said test strip comprising a first or front sheet having at least one aperture therein, said aperture having at least one included angle equal to or less than 90 degrees; a diagnostic test strip under said front sheet and extending under said aperture, said test strip containing a reagent, developable by the separate application of peroxide solution thereto, for the detection of occult blood in a stool sample to be applied to said diagnostic test strip through said aperture; a back sheet supporting said test strip in layered arrangement with said test strip and with said front sheet, said back sheet having at least one flap-covered aperture therein in that region thereof corresponding to the location of said aperture in said front sheet, whereby when the flap is opened said test strip is exposed thereunder for application of peroxide solution thereto to develop the reagent present in said test strip; and a closure flap at least partially extending over said front sheet and having closure means thereon for covering said aperture in said front sheet when in closed position.

2. A packaged diagnostic test strip as in claim 1 wherein said aperture in said front sheet is in the form of a square.

3. A packaged diagnostic test strip as in claim 1 wherein said test strip carries at least one reagent selected from the group consisting of guaicum resin, o-tolidine, and 3,3',5,5'-tetramethyl benzidine.

* * * * *